United States Patent [19]

Hamaguchi et al.

[11] Patent Number: 4,745,066
[45] Date of Patent: May 17, 1988

[54] METHOD FOR PRODUCING OPTICALLY ACTIVE GLYCOL DERIVATIVES

[75] Inventors: Shigeki Hamaguchi; Takehisa Ohashi, both of Kobe; Kiyoshi Watanabe, Akashi, all of Japan

[73] Assignee: Kanegafuchi Kagaku Kogyo Kabushiki Kaisha, Osaka, Japan

[21] Appl. No.: 846,766

[22] Filed: Apr. 1, 1986

[30] Foreign Application Priority Data

Apr. 1, 1985 [JP] Japan .................................. 60-69770

[51] Int. Cl.$^4$ ............................................ C07P 41/00
[52] U.S. Cl. ..................................... 435/280; 435/130
[58] Field of Search ................................ 435/280, 130

[56] References Cited

U.S. PATENT DOCUMENTS 4,601,987  7/1986  Klibanov et al. .................... 435/280

OTHER PUBLICATIONS

S. Iriuchijima and N. Kojima, "Asymmetric Hydrolysis of (±)-1,2-Diacetoxy-3-chloropropane and Its Related Compounds with Lipase, Synthesis of Optically Pure (S)-Propranolol," *Agric. Biol. Chem.*, 1982.

S. Iriuchijima, A. Keiyu and N. Kojima, "Asymmetric Hydrolysis of (±)-1-Acetoxy-2,3-dichloropropane with Enzymes and Microorganisms", *Agric. Biol. Chem.*, 1982.

*Primary Examiner*—Sam Rosen
*Attorney, Agent, or Firm*—Sughrue, Mion, Zinn, Macpeak & Seas

[57] ABSTRACT

A method for producing optically active glycol derivatives by biochemical resolution which comprises contacting a racemic ester of the general formula 1

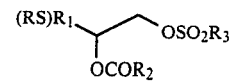

(wherein $R_1$ is an aliphatic hydrocarbon group of 1 to 16 carbon atoms, $R_2$ is an aliphatic hydrocarbon group of 1 to 8 carbon atoms, and $R_3$ is an aromatic hydrocarbon group such as phenyl, tolyl or naphtyl) with a microorganism- or animal organ-derived enzyme having stereoselective hydrolytic activity to asymmetrically hydrolyze said racemic ester of general formula 1 to produce an optically active alcohol of general formula 2*

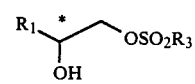

(wherein $R_1$ and $R_3$ have the same meanings as defined above) and an unreacted ester of the general formula 1*

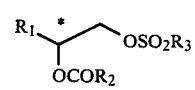

(wherein $R_1$, $R_2$ and $R_3$ have the same meanings as defined hereinbefore), separating the optically active compounds from each other, hydrolyzing said ester of general formula 1* to give an optically active glycol derivative which is antipodal to the alcohol of general formula 2* and, then, isolating the same optically active glycol derivative. The invention provides a method for producing optically active glycol derivatives, which is expedient, does not require costly reagents and is suited to commercial scale production.

10 Claims, No Drawings

METHOD FOR PRODUCING OPTICALLY ACTIVE GLYCOL DERIVATIVES

BACKGROUND OF THE INVENTION

1. Field of the Invention

The present invention relates to a method for producing optically active glycol derivatives by biochemical resolution which comprises contacting a racemic ester of the general formula 1

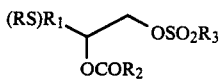

(wherein $R_1$ is an aliphatic hydrocarbon group of 1 to 16 carbon atoms, $R_2$ is an aliphatic hydrocarbon group of 1 to 8 carbon atoms, and $R_3$ is an aromatic hydrocarbon group such as phenyl, tolyl or naphthyl) with a microorganism- or animal organ-derived enzyme having stereoselective hydrolytic activity to asymmetrically hydrolyze said racemic ester of general formula 1 to produce an optically active alcohol of general formula 2*

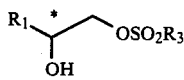

(wherein $R_1$ and $R_3$ have the same meanings as defined above) and an unreacted ester of the general formula 1*

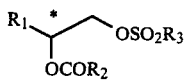

(wherein $R_1$, $R_2$ and $R_3$ have the same meanings as defined hereinbefore) and, then, isolating the respective optically active compounds.

In another aspect, the present invention further comprises a method for producing an optically active glycol derivative which comprises hydrolyzing said ester of general formula 1* to give an optically active glycol derivative which is antipodal to the alcohol of general formula 2* and, then, isolating the same optically active glycol derivative.

2. Description of the Prior Art

The optically active glycol derivatives mentioned above are versatile starting materials for the production of various optically active pharmaceutical products, agricultural chemicals and so on.

Taking 1-p-tosyloxy-2-propanol

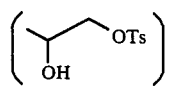

which corresponds to $R_1$=methyl and $R_3$=tolyl, as an example, it can be easily converted to propylene oxide

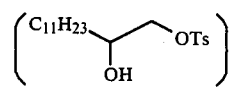

and this optically active propylene oxide can be further converted to various physiologically active substances [Uchimoto et al: Tetrahedron Letters, 3641 (1977), synthesis of (R)-recifeiolide from (R)-propylene oxide; and W. Seidel & D. Seebach: Tetrahedron Letters 23, 159 (1982), synthesis of grahamimycin $A_1$ from (R)-propylene oxide]

Further, in the case of 1-p-tosyloxy-2-tridecanol

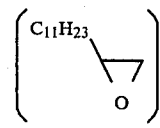

which corresponds to $R_1$=undecyl ($C_{11}H_{23}$) and $R_3$=tolyl, it can be easily converted to 1,2-epoxytridecane

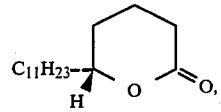

which, in turn, can be converted to δ-n-hexadecalactone

C₁₁H₂₃—... (structure shown)

an insect pheromone [J. L. Coke & A. B. Richon: Journal of Organic Chemistry 22, 3516 (1976); and Fujisawa et al: Tetrahedron Letters 26, 771 (1985)].

These optically active glycol derivatives can be respectively synthesized, for example, by means of an optically active acid after conversion to an amine or by esterifying lactic acid or 3-hydroxybutyric acid from a fermentation process, reducing the ester with a reducing agent such as lithium aluminum hydride to give 1,2-propanediol or 1,2-butanediol and introducing a sulfonic acid group into the 1-position [B. Seuring: Helvetica Chimica Acta 60, 1175 (1977)].

However, these methods are disadvantageous in that complicated procedures are involved or costly reagents must be employed, and are not suitable for commercial scale production. Therefore, the establishment of an expedient method for production of such optically active compounds has been earnestly awaited.

SUMMARY OF THE INVENTION

It is an object of the present invention to provide a commercially advantageous method for producing optically active glycol derivatives which is expedient and does not require costly reagents.

Other objects and advantages of the present invention will become apparent as the following detailed description of the invention proceeds.

DETAILED DESCRIPTION OF THE INVENTION

The present invention in one aspect thereof relates to a method for producing an optically active glycol derivative by biochemical resolution which comprises contacting a racemic ester of the general formula 1

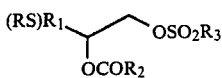
1

(wherein $R_1$ is an aliphatic hydrocarbon group of 1 to 16 carbon atoms, $R_2$ is an aliphatic hydrocarbon group of 1 to 8 carbon atoms, and $R_3$ is an aromatic hydrocarbon group) with a microorganism- or animal organ-derived enzyme having stereoselective hydrolytic activity to asymmetrically hydrolyze said racemic ester of general formula 1 to produce an optically active alcohol of general formula 2*

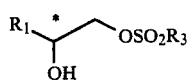
2*

(wherein $R_1$ and $R_3$ have the same meanings as defined above) and an unreacted ester of the general formula 1*

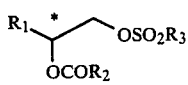
1*

(wherein $R_1$, $R_2$ and $R_3$ have the same meanings as defined hereinbefore) and, then, isolating the respective optically active compounds.

In another aspect, the present invention is directed to a method for producing an optically active glycol derivative which comprises hydrolyzing the ester of general formula 1* obtained in the first-mentioned process to give an optically active glycol derivative which is antipodal to the compound of general formula 2* and, then, isolating the same compound.

The present inventors conducted an intensive research to obtain an optically active compound by esterifying the hydroxyl group in the 2-position of an alcohol of the general formula 2

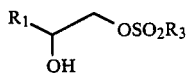
2 and permitting an enzyme having stereoselective hydrolytic activity to act on the resulting ester of general formula 1 for asymmetric hydrolysis of the ester bond. As a result, the inventors have found that certain enzymes derived from microorganisms belonging to the genera Pseudomonas, Chromobacterium, Aspergillus, Mucor, Rhizopus and so on and certain enzymes derived from animal organs such as the livers and pancreas of bovine, equine, swine, and other species of animals are respectively able to asymmetrically hydrolyze the above-mentioned ester 1 to give an unreacted ester (S)-1 having the general formula:

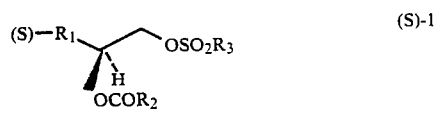
(S)-1 and an alcohol (R)-2 having the general formula:

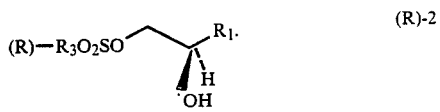
(R)-2

Further, the optically active ester 1* can be easily hydrolyzed, if necessary, into the alcohol 2* by refluxing 1* in methanol.

The products 1* and 2* can be easily separated from each other by silica gel column chromatography, for instance, so that the respective optically active compounds can be independently recovered.

The method according to the present invention will now be described in further detail.

In the ester of the general formula 1:

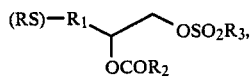
1 which is used as the substrate in the present invention, the substituent groups $R_1$, $R_2$ and $R_3$ may for example be as follows. $R_1$ is an aliphatic hydrocarbon group containing 1 to 16 carbon atoms, such as methyl, ethyl, propyl, butyl, isopropyl, undecyl, etc., preferably, being an aliphatic hydrocarbon containing 1 to 4 carbon atoms and $R_2$ may for example be an aliphatic hydrocarbon group, an unsubstituted or substituted alicyclic hydrocarbon group, or an unsubstituted or substituted phenyl or benzyl group, although an aliphatic hydrocarbon group of 1 to 8 carbon atoms is preferred from the standpoint of the enzymatically hydrolytic activity. Further, the aliphatic hydrocarbon group may be substituted by halogen and/or hydroxy groups. $R_3$ is an aromatic hydrocarbon group such as tolyl, phenyl, naphthyl and so on. These aromatic hydrocarbon groups may have halogen and/or hydroxy groups as substituents.

The starting material 1 can be synthesized, for example, by the following two routes of synthesis.

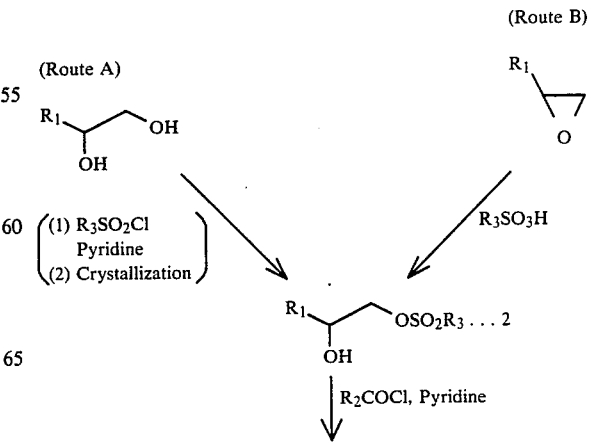

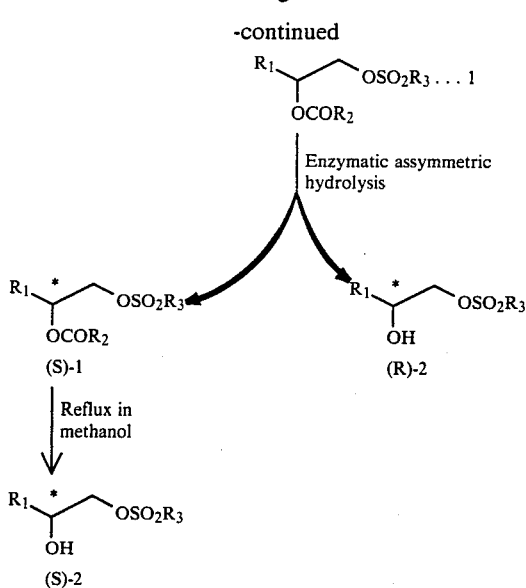

The enzyme may be any enzyme having stereoselective hydrolytic activity to asymmetrically hydrolyze the racemic ester 1 to give (S)-1 and (R)-2. Thus, for example, there may be mentioned the enzymes derived from *Pseudomonas fluorescens, Chromobacterium viscosum, Aspergillus niger, Rhizopus delemar, Rhizopus javanicus, Rhizopus japonicus* and so on. The enzymes derived from animal organs can also be used and the organs may be the pancreas, liver, etc. of bovine, equine, swine and other species of animals. Examples of commercial preparations of such enzymes that can be utilized include Lipoprotein Lipase Amano 3, Lipase AP-6, Lipase M-AP-10, Lipase D, Lipase F-AP15 and pancreatic digesting enzyme TA (all available from Amano Pharmaceutical Co., Ltd.), Saiken 100 (manufactured by Nagase Sangyo Co., Ltd.), Lipase (Carbiochem Co.), Steapsin (Wako Pure Chemical Industries, Ltd.) and so on.

The asymmetric hydrolysis reaction is conducted in the following manner. The substrate racemic ester 1 is suspended in the reaction medium at a concentration of 2 to 80 w/v percent and, then, the enzyme is added in a suitable proportion, for example in an enzyme-to-substrate weight ratio of 1:1 through 1:1000. The reaction is carried out at a temperature of 10° to 40° C., preferably in the range of 25° to 35° C. and its progress is monitored by high performance liquid chromatography (HPLC) to determine the residual amount of the substrate and the amount of product alcohol 2. The reaction is terminated when the molar ratio of 1* to 2* in the reaction system is 50:50. The pH range for this hydrolysis reaction is pH 4 to 8.5, preferably pH 6 to 7.5, but as the pH of the reaction system leans to the acidic side with the progress of reaction, this reaction is preferably carried out in a buffer solution or while the pH of the system is controlled at pH 6 to 7.5 by the addition of a neutralizing agent such as an aqueous solution of sodium hydroxide.

Depending on the types of substituents on the substrate ester, the reaction may not proceed smoothly. In such instances, the substrate may be dissolved in a suitable solvent such as dioxane, acetone, tetrahydrofuran or the like and, then, suspended in the reaction medium or if the melting point of the substrate is not so high, an elevated reaction temperature may be used for the enzymatic conversion.

Furthermore, by immobilizing the enzyme, the above asymmetric hydrolysis reaction may be conducted in repeated runs.

Following the hydrolysis reaction, the compound 1* and 2* in the reaction mixture can be separated from each other in the following manner. For example, both compounds 1* and 2* are extracted with a solvent such as methylene chloride, ethyl acetate, or the like and the extract is concentrated and subjected to silica gel chromatography. In this manner, 1* and 2* are easily separated from each other. The optically active ester 1* thus fractionated can be directly concentrated to give the ester with high optical purity. Hydrolysis of this ester in dilute hydrochloric acid at room temperature or refluxing thereof in methanol converts 1* into the alcohol 2* having the corresponding optical activity.

EXAMPLES

The following examples are intended to illustrate the present invention in further detail and should by no means be construed as limiting the scope of the invention.

EXAMPLE 1 OF PRODUCTION OF THE SUBSTRATE

Production of (RS)-2-butanoyloxy-1-p-toluenesulfonyloxypropane $1a_1$

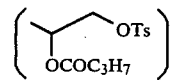

In 200 ml of methylene chloride were dissolved 38 g of 1,2-propanediol and 44 g of pyridine and, then, 95 g of p-toluenesulfonyl chloride was added gradually over a period of 15 minutes. The reaction was further conducted at room temperature for 72 hours. The reaction mixture was washed twice with one volume of water each, dehydrated over anhydrous sodium sulfate, and concentrated under reduced pressure. The concentrate was crystallized from toluene-hexane (100 ml-100 ml), filtered, and dried in vacuo to give colorless crystals of (RS)-1-p-toluenesulfonyloxy-2-propanol 2a

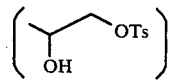

(54 g).

Melting point: 49.5°–50° C.

The $^1$H NMR (90 MHz) spectrum and elemental analysis of the above product were as follows.

$^1$H NMR (90 MHz, CDCl$_3$), δ (ppm): 1.16 (3H, d, C$\underline{H}_3$(OH)—), 2.33 (1H, broad, OH), 2.35 (3H, s, C$\underline{H}_3$—Ar), 3.70–4.18 (3H, m, —C$\underline{H}$(OH)C$\underline{H}_2$O—), 7.34, 7.80 (4H, 2d, Ar—H)

Elemental analysis: Calcd. for $C_{10}H_{14}O_4S$: C, 52.16; H, 6.13. Found: C, 52.41; H, 6.21.

In 200 ml of methylene chloride were dissolved 11.5 g of compound 2a and 6 g of triethylamine. Under ice-cooling, 6 g of butyryl chloride was added dropwise to the above solution over a period of 15 minutes and the reaction was further conducted at room temperature for 3 hours.

After butanoylation was confirmed by HPLC, the reaction mixture was washed twice with one volume of a saturated aqueous solution of sodium carbonate and concentrated under reduced pressure. The above procedure gave a syrup of (RS)-2-butanoyloxy-1-p-toluenesulfonyloxypropane (1a$_1$) in a yield of 13 g.

The $^1$H NMR (90 MHz) spectrum and elemental analysis of the above product were as follows.

$^1$H NMR (90 MHz, CDCl$_3$) δ (ppm): 0.82–1.08 (3H, t, C$\underline{H}_3$—CH$_2$—), 1.16–1.83 (5H, m, CH$_3$C$\underline{H}$(O—)—, C$\underline{H}_3$CH$_2$CH$_2$—), 2.10–2.33 (2H, t, CH$_3$CH$_2$C$\underline{H}_2$—), 2.45 (3H, s, C$\underline{H}_3$—Ar), 4.05 (2H, d, —CH(O—)C$\underline{H}_2$O—), 4.86–5.22 (1H, m, —C$\underline{H}$(O—)—), 7.35, 7.77 (4H, 2d, Ar—H).

Elemental analysis: Calcd. for C$_{14}$H$_{20}$O$_5$S: C, 55.98; H, 6.71. Found: C, 55.73; H, 6.77.

EXAMPLE 2 OF PRODUCTION OF THE SUBSTRATE

Production of (RS)-2-acetyloxy-1-p-toluenesulfonyloxypropane 1a$_2$

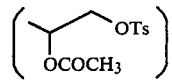

Using 2a, triethylamine and acetyl chloride, the substrate compound 1a$_2$ was produced in accordance with Example 1 of Production.

Description: Colorless crystals.
Melting point: 39.5°–40.0° C.
$^1$H NMR (90 MHz, CDCl$_3$) δ (ppm): 1.23 (3H, d, C$\underline{H}_3$CH(O—)—), 1.95 (3H, s, C$\underline{H}_3$CO—), 2.45 (3H, s, C$\underline{H}_3$—Ar—), 4.03 (2H, d, —C$\underline{H}_2$—), 4.82–5.17 (1H, m, —C$\underline{H}$—), 7.33, 7.77 (4H, 2d, Ar—H).

Elemental analysis: Calcd. for C$_{12}$H$_{16}$O$_5$S: C, 52.93; H, 5.92. Found: C, 53.08; H, 5.99.

EXAMPLE 3 OF PRODUCTION OF THE SUBSTRATE

Production of (RS)-2-butanoyloxy-1-p-toluenesulfonyloxybutane 1b

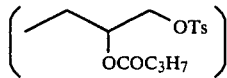

Using 1,2-butanediol, pyridine and p-toluenesulfonyl chloride, (RS)-1-p-toluenesulfonyloxy-2-butanol 2b

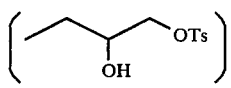

was prepared in the same manner as Example 1 of Production.

Description: Colorless crystals.
Melting point: 59°–60° C.
$^1$H NMR (90 MHz, CDCl$_3$) δ (ppm): 0.79–1.05 (3H, t, C$\underline{H}_3$CH$_2$—), 1.30–2.10 (2H, m, CH$_3$C$\underline{H}_2$—), 2.15 (1H, d, O$\underline{H}$), 2.45 (3H, s, C$\underline{H}_3$—Ar), 3.60–4.12 (3H, m, —C$\underline{H}$(OH)C$\underline{H}_2$O—), 7.30, 7.76 (4H, 2d, Ar—H)

Elemental analysis: Calcd. for C$_{11}$H$_{16}$O$_4$S: C, 54.08; H, 6.60. Found: C, 54.29; H, 6.75.

Using 2b, triethylamine and butyryl chloride, the substrate compound 1b was produced in accordance with Example 1 of Production.

Description: a syrup.
$^1$H NMR (90 MHz, CDCl$_3$) δ (ppm): 0.73–1.07 (6H, m, C$\underline{H}_3$CH$_2$CH(O—)—, C$\underline{H}_3$CH$_2$CH$_2$CO—), 1.35–1.80 (4H, m, CH$_3$C$\underline{H}_2$CH(O—)—, CH$_3$C$\underline{H}_2$CH$_2$CO—), 2.08–2.33 (2H, m, CH$_3$CH$_2$C$\underline{H}_2$CO—), 2.45 (3H, s, C$\underline{H}_3$—Ar), 4.04 (2H, d, —CH(O—)C$\underline{H}_2$O—), 4.76–5.03 (1H, m, —C$\underline{H}$(O—)—), 7.30, 7.75 (4H, 2d, Ar-H)

Elemental analysis: Calcd. for C$_{15}$H$_{22}$O$_5$S: C, 57.30; H, 7.05. Found: C, 56.95; H, 6.89.

EXAMPLE 4 OF PRODUCTION OF THE SUBSTRATE

Production of (RS)-2-butanoyloxy-1-p-toluenesulfonyloxyheptane 1c

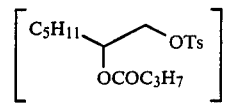

Using 1,2-heptanediol, pyridine and p-toluenesulfonyl chloride, (RS)-1-p-toluenesulfonyloxy-2-heptanol 2c

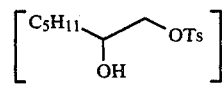

was prepared in the same manner as Example 1 of Production.

Description: a syrup.
$^1$H NMR (90 MHz, CDCl$_3$) δ (ppm): 0.70–1.75(11H, m, C$_5$H$_{11}$—), 2.45(3H, s, CH$_3$—Ar—), 2.90(1H, s, OH), 3.67(2H, d, —CH$_2$O—), 4.30–4.70 (1H, m, —CH—), 7.30, 7.77(4H, d—d, Ar—H).

Elemental analysis: Calcd. for C$_{14}$H$_{22}$O$_4$S: C, 58.72, H, 7.74. Found: C, 58.70, H, 7.71.

Using 2c, triethylamine and butyryl chloride, the substrate compound 1c was produced in accordance with Example 1 of Production.

Description: a syrup.
$^1$H NMR (90 MHz, CDCl$_3$) δ (ppm): 0.70–2.33(18H, m, C$_5$H$_{11}$, C$_3$H$_7$—), 2.42(3H, s, CH$_3$—Ar—), 3.85(2H, m, —CH$_2$O—), 4.52–4.80(1H, m, —CH—), 7.26, 7.76(4H, d—d, Ar—H).

Elemental analysis: Calcd. for C$_{18}$H$_{28}$O$_5$S: C, 60.65, H, 7.92. Found: C 60.71, H, 7.94.

EXAMPLE 5 OF PRODUCTION OF THE SUBSTRATE

Production of (RS)-2-butanoyloxy-1-p-toluenesulfonyloxyhexadecane 1d

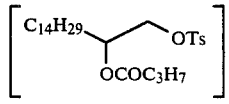

Using 1,2-hexadecanediol, pyridine and p-toluenesulfonyl chloride, (RS)-1-p-toluenensulfonyloxy-2-hexadecanol 2d

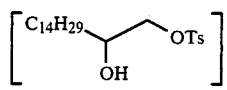

was prepared in the same manner as Example 1 of Production.

Description: a syrup.

$^1$H NMR (90 MHz, CDCl$_3$) δ (ppm): 0.75–1.73(29H, m, C$_{14}$H$_{29}$—), 2.00(1H, S, OH), 2.45 (3H, s, CH$_3$—Ar), 3.67(2H, d, —CH$_2$O—), 4.40–4.70 (1H, m, —CH—), 7.26, 7.76(4H, d—d, Ar—H).

Elemental analysis: calcd. for C$_{23}$H$_{40}$O$_4$S: C, 66.95, H, 9.77. Found: C, 66.99, H, 9.82.

Using 2d, triethylamine and butyryl chloride, the substrate compound 1d was prepared in accordance with Example 1 of Production.

Description: a syrup.

$^1$H NMR (90 MHz, CDCl$_3$) δ (ppm): 0.80–2.27(36H, m, C$_{14}$H$_{29}$—, C$_3$H$_7$—), 2.44(3H, s, CH$_3$—Ar), 3.90–4.27(1H, m, —CH$_2$O—), 4.56–4.79(2H, m, —CH—), 7.27, 7.73(4H, d—d, Ar—H).

Elemental analysis: Calcd. for C$_{27}$H$_{46}$O$_5$S; C, 67.18, H, 9.60. Found: C, 67.25, H, 9.67.

EXAMPLES 1 TO 16

A 20 ml test tube equipped with a cap was charged with 100 mg of the substrate compound 1a$_1$ or 1b, 10 mg of the enzyme and 5 ml of 0.1M phosphate buffer (pH 7.25) and shaken at 33° C. for 48 hours. To the reaction mixture was then added 10 ml of ethyl acetate to extract the unreacted ester (1a$_1$ or 1b) and the hydrolysate (2a or 2b). The ethyl acetate layer was dehydrated, filtered, and subjected to high performance liquid chromatography using a chiral column to determine the yield and optical purity of the alcohol. The results are shown in Table 1.

The conditions of analysis and the retention time values were as follows.

Liquid chromatography
Column: Chiral CEL OC (Nippon Bunko).
Developer solvent system: hexane-isopropyl alcohol =95:5.
Flow rate: 2.5 ml/min.
Detection: UV, 235 nm.
Retention times:
  (RS)—1a$_1$: 10.7 minutes
  (S)—2a: 32.1 minutes
  (R)—2a: 27.4 minutes
  (RS)—1b: 8.4 minutes
  (S)—2b: 19.8 minutes
  (R)—2b: 17.6 minutes.

Incidentally, as to compounds 1a$_1$ and 1b, the R-form and the S-form have the same retention time and are, therefore, not separated from each other.

TABLE 1

| Example No. | Enzyme | Origin | Substrate | The percentage of product alcohol relative to added substrate, max. 50% | Optical purity (% e.e.) |
|---|---|---|---|---|---|
| 1 | Lipoprotein lipase Amano 3 | Pseudomonas fluorescens | 1a$_1$ | 50 | >99 |
| 2 | Lipase | Chromobacterium viscosum | " | 27 | >99 |
| 3 | Lipase AP-6 | Aspergillus niger | " | 3 | >99 |
| 4 | Lipase M-AP-10 | Mucor sp. | " | 5 | >99 |
| 5 | Lipase D | Rhizopus delemar | " | 15 | >99 |
| 6 | Lipase F-AP 15 | Rhizopus javanicus | " | 13 | >99 |
| 7 | Saiken 100 | Rhizopus japonicus | " | 8 | >99 |
| 8 | Pancreatic digesting enzyme TA | Swine pancreas | " | 9 | 72 |
| 9 | Lipoprotein lipase Amano 3 | Pseudomonas fluorescens | 1b | 50 | >99 |
| 10 | Lipase | Chromobacterium viscosum | " | 32 | >99 |
| 11 | Lipase AP-6 | Aspergillus niger | " | 9 | >99 |
| 12 | Lipase M-AP-10 | Mucor sp. | " | 18 | >99 |
| 13 | Lipase D | Rhizopus delemar | " | 30 | >99 |
| 14 | Lipase F-AP 15 | Rhizopus japonicus | " | 17 | >99 |
| 15 | Saiken 100 | Rhizopus japonicus | " | 11 | >99 |
| 16 | Pancreatic digesting enzyme TA | Swine pancreas | " | 11 | 60 |

EXAMPLE 17

The reaction was conducted using Lipoprotein lipase Amano 3 which possessed the highest hydrolytic activity among the lipases in Examples 1 to 16.

To 30 ml of 0.1M phosphate buffer (pH 7.25) were added to 3.0 g of the substrate 1a$_1$ and 0.03 g of Lipoprotein lipase Amano 3 and the asymmetric hydrolysis reaction was conducted at 33° C. with stirring for 4 hours, while the reaction system was controlled at pH 7.25 using an 1N aqueous solution of NaOH. The reaction mixture (30 ml) was extracted twice with 60 ml portions of methylene chloride and the methylene chloride layers were combined, dehydrated over anhydrous sodium sulfate and concentrated under reduced pressure. The concentrate was subjected to silica gel column chromatography (Wakogel C-200, L/D=40/1.5 cm, developer solvent: hexane-acetone=12-6:1, v/v) and the fractions corresponding to the ester (S)-1a$_1$ and the alcohol (R)-2a were recovered and concentrated under reduced pressure. The above procedure gave 1.15 g of (S)-1a₁ (yield 77%) and 0.91 g of (R)-2a (yield 79%).

The above (R)-2a was further recrystallized from ether-hexane to obtain 0.70 g (theoretical yield based on (RS)-1a₁:61%).

The optical rotation values of the two compounds were as follows.

(S)-1a₁: $[\alpha]_D^{20} -10.0°$ (c=2.0, chloroform).
(R)-2a: $[\alpha]_D^{20} -12.6°$ (c=2.0, chloroform).

The literature value: B. Seuring et al (Helvetica Chimica Acta 60, 1175 (1977): (S)-2a: $[\alpha]_D = +11.3°$ (c=1.1, chloroform).

Then, the ester (S)-1a₁ was refluxed in methanol for 3 hours, whereby it was converted into the alcohol (S)-2a. The reaction mixture was concentrated under reduced pressure to remove the methanol and the concentration residue was washed with a saturated aqueous solution of sodium hydrogen carbonate, extracted with methylene chloride, dehydrated and concentrated to give (S)-2a in a yield of about 75%. The optical rotation value of this product was as follows.

(S)-2a: $[\alpha]_D^{20} +12.6°$ (c=2.0, chloroform).

EXAMPLES 18 AND 19

Using 1a₂ or 1b, the asymmetric hydrolysis reaction was conducted and (S)-1a₂ and (R)-2a or (S)-1b and (R)-2b were respectively separated and isolated as in Example 17. The results are shown in Table 2.

TABLE 2

| Example No. | Substrate | (S)-ester | | | (R)-alcohol | | |
|---|---|---|---|---|---|---|---|
| | | Yield (%)(*d) | $[\alpha]_D^{20(*a)}$ | % e.e.(*b) | Yield (%) | $[\alpha]_D^{20}$ | % e.e. |
| 17 | 1a₁ | 39 | −10.0° | >99 | 31 | −12.6° | >99 |
| 18 | 1a₂(*c) | 35 | −13.0° | >99 | 40 | −12.0° | >99 |
| 19 | 1b | 40 | −18.3° | >99 | 40 | −9.4° | >99 |

Conditions of reaction:
3.0 g of the substrate and 0.03 g of Lipoprotein lipase Amano 3 in 30 ml of 0.1 M phosphate buffer (pH 7.25). The reaction was conducted at 33° C. for 4 hours.
(*a)$[\alpha]_D^{20}$ (c = 2.0, chloroform)
(*b)Each ester was hydrolyzed by refluxing in methanol and the resulting alcohol was assayed by high performance liquid chromatography using a chiral column.
(*c)Reaction temperature: 40° C.
(*d)The percentage of ester or alcohol is calculated from added substrate (max. 50%).

EXAMPLES 20 AND 21

Using 1c, and 1d, the asymmetric hydrolysis reaction was performed. The hydrolysis proceeded approximately 70% based on (RS)-1c and 1d. All other preparations were performed according to Example 17. The results are shown in Table 3.

TABLE 3

| Example No. | Substrate | Ester | | Alcohol | |
|---|---|---|---|---|---|
| | | Yield (%)(*d) | $[\alpha]_D^{20}$ (C = 4, Methanol) | Yield (%) | $[\alpha]_D^{20}$ (C = 4, Methanol) |
| 20 | (RS)-1c | 24 | −0.95° | 58 | 0.74° |
| 21 | (RS)-1d | 21 | −0.92° | 60 | −0.85° |

Conditions of reaction:
3.0 g of the substrate and 0.3 g of Lipoprotein lipase Amano 3 in 30 ml of 0.1 M phosphate buffer (pH 7.25). The reaction was conducted at 33° C. for 4 hours.
(*d)The percentage of ester or alcohol is calculated from added substrate (max. 50%).

What is claimed is:

1. A method for producing optically active glycol derivatives by biochemical resolution which comprises contacting a racemic ester of the general formula 1

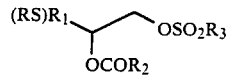

(wherein R₁ is an aliphatic hydrocarbon group of 1 to 16 carbon atoms, R₂ is an aliphatic hydrocarbon group of 1 to 8 carbon atoms, and R₃ is a phenyl, tolyl or naphtyl group) with a microorganism- or animal organ-derived enzyme having stereoselective, hydrolytic activity to asymmetrically hydrolyze said racemic ester of general formula 1 to produce an optically active alcohol of general formula 2*

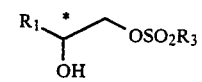

(wherein R₁ and R₃ have the same meanings as defined above) and an unreacted ester of the general formula 1*

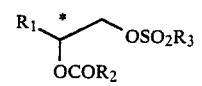

(wherein R₁, R₂ and R₃ have the same meanings as defined hereinbefore) and, then, isolating the respective optically active compounds.

2. A method according to claim 1, wherein the substituent group R₁ is an aliphatic hydrocarbon group containing 1 to 4 carbon atoms.

3. A method according to claim 1 or 2 wherein the hydrolysate alcohol 2* is represented by the general formula

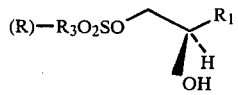

(wherein R₁ and R₃ have the same meanings as defined) and the unreacted ester 1* is represented by the general formula

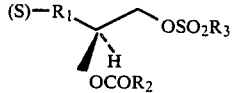

(wherein R₁, R₂ and R₃ have the same meanings as defined).

4. A method according to claim 1, 2 or 3, wherein the microorganism-derived enzyme is an enzyme derived from a microorganism belonging to any of the genera Pseudomonas, Chromobacterium, Aspergillus, Mucor and Rhizopus.

5. A method according to claim 1, 2 or 3, wherein the animal organ-derived enzyme is an enzyme derived from bovine or swine liver or pancreas.

6. A method for producing optically active glycol derivatives by biochemical resolution which comprises contacting an ester of the general formula 1

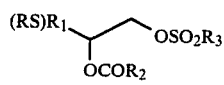
       1

(wherein $R_1$ is an aliphatic hydrocarbon group of 1 to 16 carbon atoms, $R_2$ is an aliphatic hydrocarbon group of 1 to 8 carbon atoms, and $R_3$ is a phenyl, tolyl or naphtyl group) with a microorganism- or animal organ-derived enzyme having stereoselective hydrolytic activity to asymmetrically hydrolyze said racemic ester of general formula 1 to produce an optically active alcohol of general formula 2*

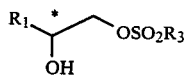
       2*

(wherein $R_1$ and $R_3$ have the same meanings as defined above) and an unreacted ester of the general formula 1*

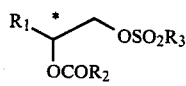
       1*

(wherein $R_1$, $R_2$ and $R_3$ have the same meanings as defined hereinbefore), separating the optically active compounds from each other, hydrolyzing said ester of general formula 1* to give an optically active glycol derivative which is antipodal to the alcohol of general formula 2* and, then, isolating the same optically active glycol derivative.

7. A method according to claim 6, wherein the substituent group $R_1$ is an aliphatic hydrocarbon containing 1 to 4 carbon atoms.

8. A method according to claim 6 or 7, wherein the hydrolysate alcohol 2* is represented by the general formula

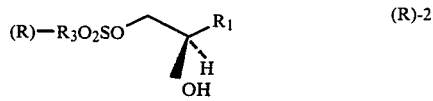
       (R)-2

(wherein $R_1$ and $R_3$ have the same meanings as defined) and the unreacted ester 1* is represented by the general formula

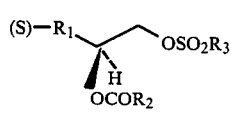
       (S)-1

(wherein $R_1$, $R_2$ and $R_3$ have the same meanings as defined).

9. A method according to claim 6, 7 or 8, wherein the microorganism-derived enzyme is an enzyme derived from a microorganism belonging to any of the genera Psuedomonas, Chromobacterium, Aspergillus, Mucor and Rhizopus.

10. A method according to claim 6, 7 or 8, wherein the animal organ-derived enzyme is an enzyme derived from bovine or swine liver or pancreas.

* * * * *